United States Patent
Kovalsky et al.

(10) Patent No.: US 10,945,841 B2
(45) Date of Patent: Mar. 16, 2021

(54) VALVE PROSTHESIS AND METHOD FOR DELIVERY

(71) Applicant: MEDTRONIC, INC., Minneapolis, MN (US)

(72) Inventors: Igor Kovalsky, Mounds View, MN (US); Ilia Hariton, Zihron (IL); Yossi Tuval, Yehuda (IL); Nadav Yellin, Irvine, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 16/248,564

(22) Filed: Jan. 15, 2019

(65) Prior Publication Data
US 2019/0142588 A1 May 16, 2019

Related U.S. Application Data

(62) Division of application No. 14/748,693, filed on Jun. 24, 2015, now Pat. No. 10,213,302, which is a division of application No. 13/736,494, filed on Jan. 8, 2013, now Pat. No. 9,066,801.

(51) Int. Cl.
*A61F 2/24* (2006.01)

(52) U.S. Cl.
CPC .......... *A61F 2/2445* (2013.01); *A61F 2/2418* (2013.01); *A61F 2210/0061* (2013.01); *A61F 2230/0065* (2013.01); *A61F 2250/006* (2013.01); *A61F 2250/0039* (2013.01)

(58) Field of Classification Search
CPC .................. A61F 2/24; A61F 2/2445
See application file for complete search history.

(56) References Cited

U.S. PATENT DOCUMENTS

| 5,415,667 A | 5/1995 | Frater |
| 5,545,215 A | 8/1996 | Duran |
| 6,562,069 B2 | 5/2003 | Cai et al. |
| 7,101,396 B2 | 9/2006 | Artof et al. |
| 7,399,315 B2 | 7/2008 | Iobbi |
| 2003/0069635 A1 | 4/2003 | Cartledge et al. |
| 2005/0137682 A1 | 6/2005 | Justino |
| 2007/0055350 A1 | 3/2007 | Erickson et al. |

(Continued)

FOREIGN PATENT DOCUMENTS

| CN | 102098983 A | 6/2011 |
| CN | 12333500 A | 1/2012 |

(Continued)

OTHER PUBLICATIONS

Communitcation Article 94(3), European Patent Application No. 18170073.3, 1-4 pgs.

(Continued)

*Primary Examiner* — Matthew W Schall
(74) *Attorney, Agent, or Firm* — Medler Ferro Woodhouse & Mills PLLC

(57) ABSTRACT

Heart valve prostheses are provided for replacing a cardiac valve. The heart valve prosthesis includes a self-expanding frame including a first portion and a second portion. In the collapsed configuration, the first portion is positioned adjacent to the second portion. In the expanded configuration, the first portion moves to be positioned within an interior area of the second portion.

20 Claims, 13 Drawing Sheets

(56) References Cited

U.S. PATENT DOCUMENTS

| | | |
|---|---|---|
| 2008/0033543 A1 | 2/2008 | Gurskis et al. |
| 2008/0071368 A1 | 3/2008 | Tuval et al. |
| 2009/0054973 A1 | 2/2009 | Johnson |
| 2010/0262231 A1 | 10/2010 | Tuval et al. |
| 2011/0137397 A1 | 6/2011 | Chau et al. |
| 2011/0208283 A1 | 8/2011 | Rust |
| 2011/0218619 A1 | 9/2011 | Benichou et al. |
| 2012/0022640 A1 | 1/2012 | Gross et al. |
| 2013/0204360 A1* | 8/2013 | Gainor ............... A61F 2/2403 623/2.18 |

FOREIGN PATENT DOCUMENTS

| | | |
|---|---|---|
| CN | 102438546 B | 5/2012 |
| CN | 104540473 A | 4/2015 |
| EP | 2537487 B1 | 12/2012 |
| EP | 2 809 272 A1 | 12/2014 |
| GB | 2398245 B | 8/2004 |
| WO | 2008/097589 A1 | 8/2008 |
| WO | 2011/106137 A1 | 9/2011 |
| WO | 2011/143263 A2 | 9/2011 |
| WO | 2012/177942 A2 | 12/2012 |
| WO | 2012173995 A2 | 9/2013 |

OTHER PUBLICATIONS

Chinese Notice of First Office Action and Search Report, Appln No. 201480004177.7.

Communication Article 94(3), European Patent Application No. 14701852.7, 1-5 pgs.

Extended Search Report dated Jul. 5, 2018 in corresponding European Patent Application No. 18 170 073.3.

Office Action dated May 25, 2020 in Chinese Application No. 20181053467.6.

* cited by examiner

VALVE PROSTHESIS AND METHOD FOR DELIVERY

CROSS-REFERENCE TO RELATED APPLICATION

This application is a divisional of U.S. application Ser. No. 14/748,693 filed Jun. 24, 2015, which is a divisional of U.S. application Ser. No. 13/736,494 filed Jan. 8, 2013, now U.S. Pat. No. 9,066,801, the disclosures of which are incorporated by reference herein in their entirety.

BACKGROUND OF THE INVENTION

Field of the Invention

The present invention is related to an artificial heart valve frame. More specifically, the present invention is directed to an artificial valve prosthesis.

Background Art

The mitral valve is a functional organ composed of multiple dynamically interrelated units. During cardiac cycle, the fibrous skeleton, the anterior and posterior leaflets, the papillary muscles, the chordae tendinea, and the ventricular and atrial walls all interplay to render a competent valve. The complex interaction between the mitral valve and the ventricle by the subvalvular apparatus (the papillary muscles and the chordae tendinea) is essential in maintaining the continuity between the atrio-ventricular ring (which is part of the fibrous skeleton of the heart) and the ventricular muscle mass, which provides for the normal functioning of the mitral valve.

Cardiac valves, including the mitral valve, exhibit two types of pathologies: regurgitation and stenosis. In the case of the mitral valve, regurgitation is the abnormal leaking of blood from the left ventricle, through the mitral valve, and into the left atrium, when the left ventricle contracts. Stenosis is the narrowing of the orifice of the mitral valve of the heart. Regurgitation is the more common of the two defects. Either defect can be treated by a surgical repair. However, surgical procedures can lead to an interruption of the mitral annulus-papillary muscle continuity, which accounts for changes in geometry mechanics and performance of the left ventricle. These problems are lessened by the emerging techniques for minimally invasive mitral valve repair, but still many of those techniques require arresting the heart and funneling the blood through a heart-lung machine, which can also be traumatic for patients.

Under certain conditions, the cardiac valve must be replaced. Standard approaches to valve replacement require cutting open the patient's chest and heart to access the native valve. Such procedures are traumatic to the patient, require a long recovery time, and can result in life threatening complications. Therefore, many patients requiring cardiac valve replacement are deemed to pose too high a risk for open heart surgery due to age, health, or a variety of other factors. These patient risks associated with heart valve replacement are lessened by the emerging techniques for minimally invasive valve repair, but still many of those techniques require arresting the heart and passing the blood through a heart-lung machine.

In addition, valve replacement can create additional problems including limitation of the mitral flow during exercise due to a small effective orifice area and high cardiac output imposed by a smaller size artificial valve. Further, the rigid structure of an artificial valve prevents the physiologic contraction of the posterior wall of the left ventricle surrounding the mitral annulus during systole. Also, myocardial rupture can result from excision or stretching of the papillary muscle in a thin and fragile left ventricle. Additionally, chordae rupture can also occur due to the chordae rubbing against the artificial valve over time, leading to increased heart wall stress. It has been shown that severing the chordae can lead to a 30% reduction in chamber function. Thus, mitral valve replacement has a high mortality rate in very sick, chronic heart failure patients.

The chordae tendinea, which connect the valve leaflets to the papillary muscles (PM) act like "tie rods" in an engineering sense. Not only do the chordae tendinea prevent prolapse of the mitral valve leaflets during systole, but they also support the left ventricular muscle mass throughout the cardiac cycle. To function adequately, the mitral valve opens to a large orifice area and, for closure, the mitral leaflets have an excess surface area (i.e. more than needed to effectively close the mitral orifice). On the other hand, systolic contraction of the posterior ventricular wall around the mitral annulus (MA) creates a mobil D-shaped structure with sphincter-like function which reduces its area by approximately 25% during systole, thus exposing less of the mitral leaflets to the stress of the left ventricular pressure and flow.

It has been long postulated that the structural integrity of the MA-PM continuity is essential for normal left ventricular function. Recent evidence supports the concept that preservation of the subvalvular apparatus with the MA-PM continuity in any procedure on the mitral valve is important for the improved long-term quality and quantity of life following valve replacement. Maintaining the MA-PM continuity, thus, appears to provide a substantial degree of protection from the complications associated with valve replacement.

Efforts have been focused on percutaneous transluminal delivery of replacement cardiac valves to solve the problems presented by traditional open heart surgery and minimally-invasive surgical methods. In such methods, a valve prosthesis is compacted for delivery in a catheter and then advanced through a patient's vasculature to the heart, where the prosthesis is then deployed in the native valve annulus.

Therefore, what is needed is a mitral valve prosthesis and method of implantation that minimizes the traumatic impact on the heart while effectively replacing native leaflet function. A consistent, reproducible, and safe method to introduce a prosthesis into the mitral position in a minimally invasive fashion could be attractive for numerous reasons: a) it can treat both functional and degenerative mitral regurgitation (MR); b) it can treat mitral stenosis; c) it can offer a remedy to inoperable patients, high risk surgical patients, and those that cannot tolerate bypass; d) it can allow a broad range of practitioners to perform mitral valve procedures; and/or e) it can enable more consistency in measuring outcome.

BRIEF SUMMARY OF THE INVENTION

Provided herein are mitral valve prostheses and methods for implanting the prostheses in the heart. The prostheses generally include a self-expanding frame and two or more support arms. A valve prosthesis is sutured to the self-expanding frame. Each support arm corresponds to a native mitral valve leaflet. At least one support arm immobilizes the native leaflets, and holds the native leaflets close to the main frame. Such configuration achieves numerous goals. For example, such configuration achieves one or more of the following: prevents the native leaflets from obstructing flow through the left ventricular outflow tract (LVOT); prevents the native leaflets from interacting with the prosthetic leaflets; recruits the native leaflets in minimizing peri-valvular leaks; maintains proper alignment of the valve prosthesis; avoid systolic anterior mobility; and maintains valve stability by preventing migration of the valve into the atrium or ventricle and prevents damage to the native chordae. Additionally, the prosthetic mitral valve frame can include two or more anchor attachment points. Each anchor attachment point can be attached to one or more anchors that help attach the mitral valve to the heart. Such configuration provides added stability to the prosthetic mitral valve and prevents damage to the native chordae. The design of the prosthesis also mimics the native valve and supports a non-circular in vivo configuration, which better reflects native valve function.

In view thereof, disclosed herein are aspects of a valve prosthesis which is generally designed to include a main frame including a first section, a second section, and a third section; a valve body connected to the frame, and a support frame including a first engagement arm and a second engagement arm connected to the main frame in the first section, where the first engagement arm is connected to the main frame in the first section at a first point and a second point, where in the second engagement arm is connected to the main frame in the first section at a third point and a fourth point, and where the first engagement arm and the second engagement arm include a radial portion where the respective arms extend in the radial direction.

In another exemplary aspect, disclosed herein are aspects of a valve prosthesis which is generally designed to include a valve body and a frame including a first portion connected to the valve body and a second portion adapted for implantation in a native valve annulus, the frame having a delivery configuration where the first portion is longitudinally adjacent to the second portion and an expanded configuration where the first portion is positioned within an interior area of the second portion.

In another exemplary embodiment, disclosed herein are aspects of a method of treating a valve disorder in a patient's heart which generally includes collapsing a valve prosthesis including a frame onto a delivery system to place a first portion of the frame adjacent a second portion of the frame, delivering the delivery system and valve prosthesis to a heart, expanding the valve prosthesis in the heart such that the first portion of the frame moves to be positioned within an interior area of the second portion of the frame, and withdrawing the delivery system from the heart.

BRIEF DESCRIPTION OF THE DRAWINGS/FIGURES

The accompanying figures, which are incorporated herein, form part of the specification and illustrate embodiments of a valve prosthesis frame and delivery system. Together with the description, the figures further serve to explain the principles of and to enable a person skilled in the relevant art(s) to make, use, and implant the valve prosthesis described herein. In the drawings, like reference numbers indicate identical or functionally similar elements.

DETAILED DESCRIPTION OF THE INVENTION

The following detailed description of a valve prosthesis and valve prosthesis frame refers to the accompanying figures that illustrate exemplary embodiments. Other embodiments are possible. Modifications can be made to the embodiments described herein without departing from the spirit and scope of the present invention. Therefore, the following detailed description is not meant to be limiting.

The present invention is directed to a heart valve prosthesis having a self-expanding frame that supports a valve body. The valve prosthesis can be delivered percutaneously to the heart to replace the function of a native valve. For example, the valve prosthesis can replace a bicuspid or a tricuspid valve such as the aortic, mitral, pulmonary, or tricuspid heart valve. As used herein the term "distal" is understood to mean downstream to the direction of blood flow. The term "proximal" is intended to mean upstream to the direction of blood flow.

In one aspect of the invention, the valve body comprises three leaflets that are fastened together at enlarged lateral end regions to form commissural joints, with the unattached edges forming the coaptation edges of the valve. The leaflets can be fastened to a skirt, which in turn can be attached to the frame. The upper ends of the commissure points define an outflow or proximal portion of the valve prosthesis. The opposite end of the valve at the skirt defines an inflow or distal portion of the valve prosthesis. The enlarged lateral end regions of the leaflets permit the material to be folded over to enhance durability of the valve and reduce stress concentration points that could lead to fatigue or tearing of the leaflets. The commissural joints are attached above the plane of the coaptation edges of the valve body to minimize the contacted delivery profile of the valve prosthesis. The base of the valve leaflets is where the leaflet edges attach to the skirt and the valve frame.

Referring now to FIGS. 1-4, frame 100 is an exemplary aspect of the present invention. Frame 100 includes an inner portion 110, an outer portion 120, and connecting arms 130 connecting inner portion 110 to outer portion 120. Inner portion 110 and outer portion 120 in frame 100 include a plurality of cells that form a cell pattern. The plurality of cells can be different sizes and/or shapes.

Figure 17:
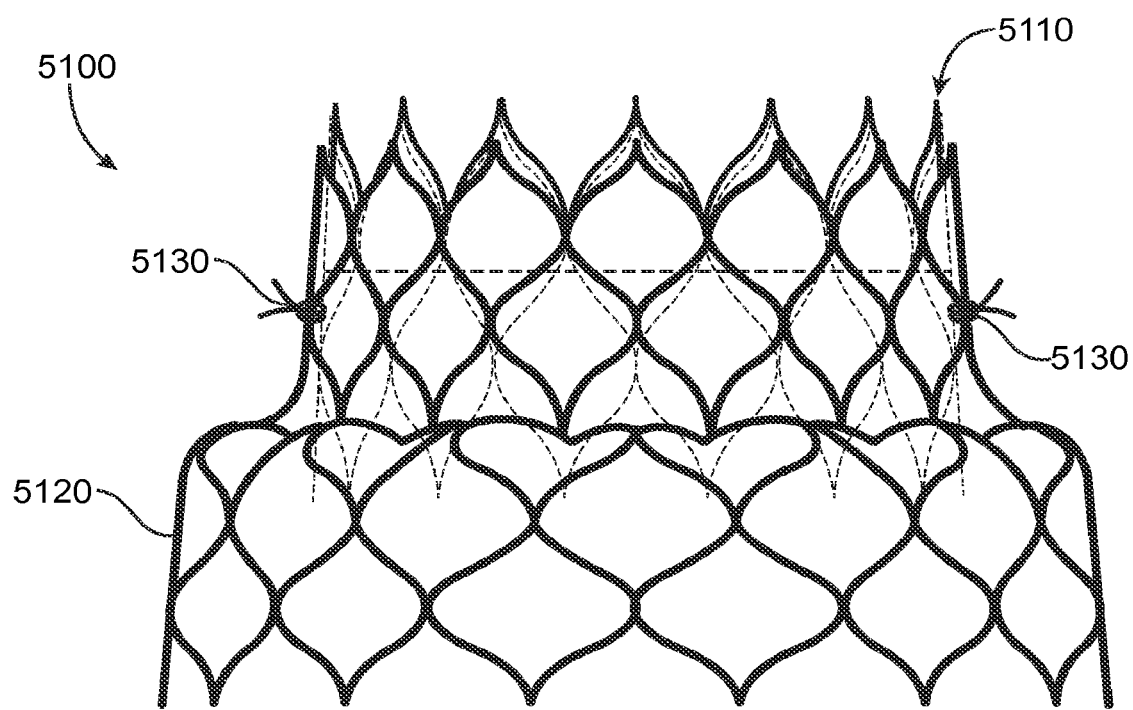
FIG. 17 is a front view of a valve prosthesis frame according to an aspect of this disclosure.

Inner portion 110 can be configured to be expandable. In one aspect of the invention, inner portion 110 is self-expandable and can be formed of a shape memory alloy such as NITINOL. Other biocompatible metals can also be used. Outer portion 120 can also be formed of a shape memory alloy such as NITINOL, or other biocompatible metals. Inner portion 110 and outer portion 120 can be integrally formed and connected by connecting arms 130. Connecting arms 130 can also be formed of a shape memory alloy such as NITINOL, or other biocompatible metals. In an alternate aspect of the invention, the inner portion and the outer portion of the frame can comprise separate modular components that are attached to one another, for example as shown in FIG. 17. As shown in FIG. 17, inner portion 5110 is attached to outer portion 5120 by connections 5130 to form frame 5100.

In one aspect of the invention, inner portion 110 is designed to flex and deform so as to mimic the natural cardiac movements of the heart through the cardiac cycle. In another aspect of the invention, inner portion 110 is designed in a rigid fashion to avoid flexing or deformation during the cardiac cycle.

Frame 100 can be attached to valve 200 to form valve prosthesis 10. Valve 200 can include leaflets 210 and a covering 220. In one aspect of the invention, covering 220 is a biocompatible fabric or other biocompatible material. In an alternate aspect of the invention, covering 220 can be tissue, for example bovine or porcine pericardium. In one aspect of the invention, valve 200 is connected to frame 100 in inner portion 110. The object of the present valve prosthesis is to mimic the native valve structure. In one aspect of the invention, valve 200 can be sewn onto inner portion 110 as described in U.S. Patent Application Publication No. 2008/0071368, which is incorporated herein by reference in its entirety. In one aspect of the disclosure, valve 200 can be formed of a biocompatible synthetic material, synthetic polymer, an autograft tissue, xenograft tissue, or other alternative materials. In a further aspect of the invention, valve 200 can be a tri-leaflet bovine pericardium valve, a bi-leaflet valve, or any other suitable valve.

Outer portion 120 can be formed in a straight fashion (i.e., cylindrical and parallel to the longitudinal axis of frame 100) or in a flared fashion (i.e., diverging away from the longitudinal axis of frame 100). In one aspect of the invention, outer portion 120 bulges outward from inner portion 110. In a further aspect of the invention, outer portion 120 can be an elliptical shape. In a further aspect, the proximal end of outer portion 120 is flared outward. In one aspect of the disclosure, outer portion 120 is wider than the native valve at the native valve annulus. Such a configuration prevents migration of prosthesis 10 into the ventricle and improves sealing of prosthesis 10 against the atrial wall. In an aspect of the invention, outer portion 120 can have an hourglass profile.

In one aspect of the invention, inner portion 110 can be approximately 17 mm to approximately 40 mm in diameter. In a further aspect of the invention, outer portion 120 can be approximately 30 mm to approximately 70 mm in diameter.

The plurality of cells forming a cell pattern in frame 100 permit frame 100 to adapt to the specific anatomy of the patient, thereby reducing the risk of valve prosthesis migration and reducing the risk of perivalvular leakage. In one aspect of the invention, valve prosthesis 10 is configured to be disposed in the mitral annulus of a patient's left ventricle.

Typically, heart valve prostheses aim to create laminar blood flow through the prosthesis in order to prevent lysis of red blood cells, stenosis of the prosthesis, and other thromboembolic complications. Outer portion 120 is designed to conform to a patient's anatomy and to anchor valve prosthesis 10 in the patient's natural valve annulus to prevent lateral movement or migration of valve prosthesis 10 due to normal movement of the heart.

Inner portion 110 is configured to be expandable and can be self-expandable. Inner portion 110 can be formed of a shape memory alloy such as NITINOL. Other biocompatible metals can also be used. Outer portion 120 can also be formed of a shape memory alloy such as NITINOL, or other biocompatible metals. Inner portion 110 and outer portion 120 can be integrally formed. In this aspect, inner portion 110 is connected to outer portion 120 with connecting arms 130. In an alternate aspect of the invention, inner portion 110 and outer portion 120 can comprise separate modular components that are attached to one another. In one aspect of the invention, inner portion 110 is designed to flex and deform so as to mimic the natural cardiac movements of the heart through the cardiac cycle. In another embodiment, inner portion 110 is designed in a rigid fashion to avoid flexing or deformation during the cardiac cycle.

Figure 3:
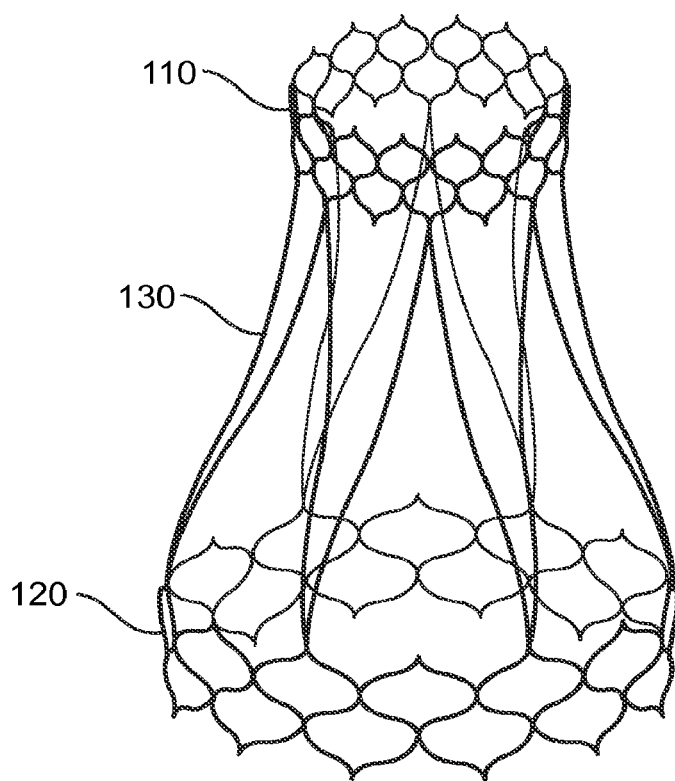
FIG. 3 is a perspective view of a valve prosthesis frame according to an aspect of this disclosure.
Figure 4:
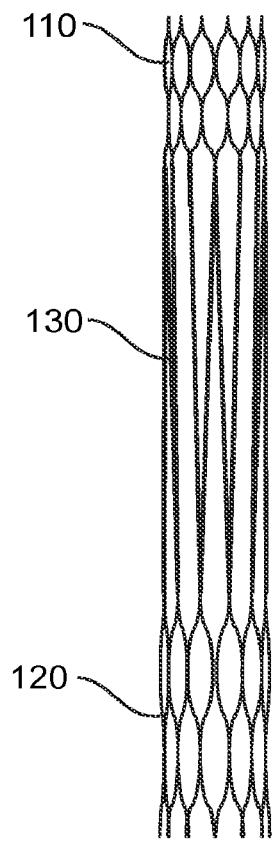
FIG. 4 is a front view of a valve prosthesis frame according to an aspect of this disclosure.
Figure 5:
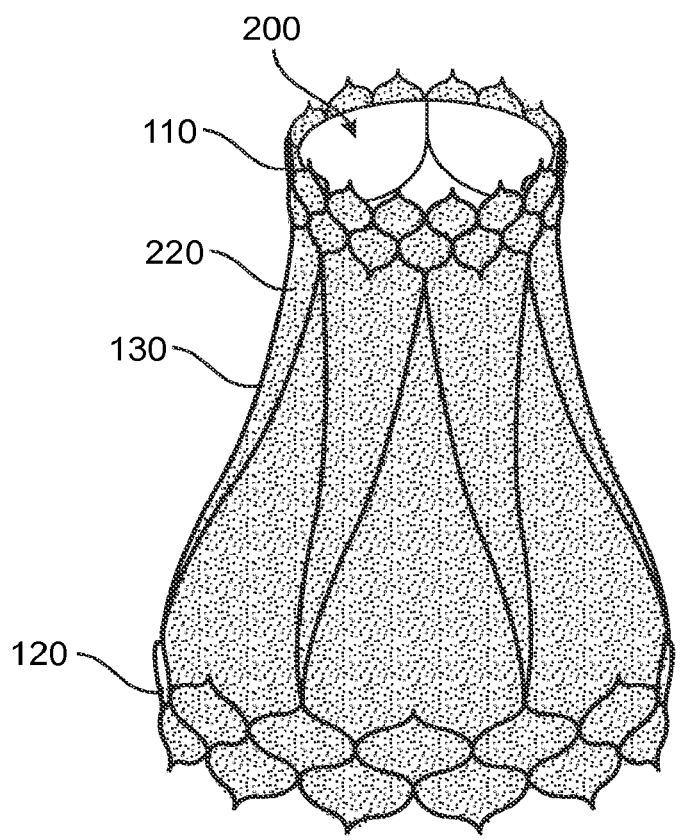
FIG. 5 is a perspective view of a valve prosthesis according to an aspect of this disclosure.

In order to deploy valve prosthesis 10 in a patient's native valve, valve prosthesis 10 can be compacted and loaded onto a delivery device for advancement through a patient's vasculature. In the collapsed configuration, inner portion 110 and outer portion 120 are positioned in series such that inner portion 110 is adjacent outer portion 120 along the longitudinal axis. FIGS. 3-4 illustrate the relative positioning between inner portion 110, outer portion 120 and connecting arms 130 in the collapsed configuration. In the collapsed configuration, inner portion 110 is longitudinally positioned at a first end of frame 100, outer portion 120 is longitudinally positioned at a second end of frame 100, and connecting arms 130 are longitudinally positioned between inner portion 110 and outer portion 120.

Figure 1:
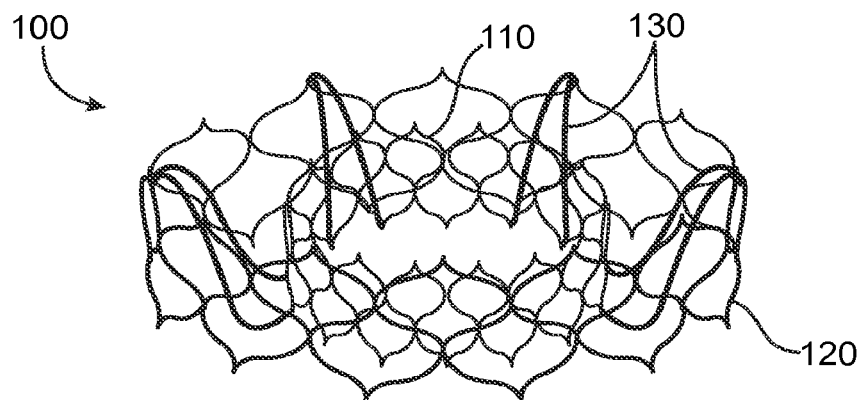
FIG. 1 is a perspective view of a valve prosthesis frame according to an aspect of this disclosure.
Figure 2:
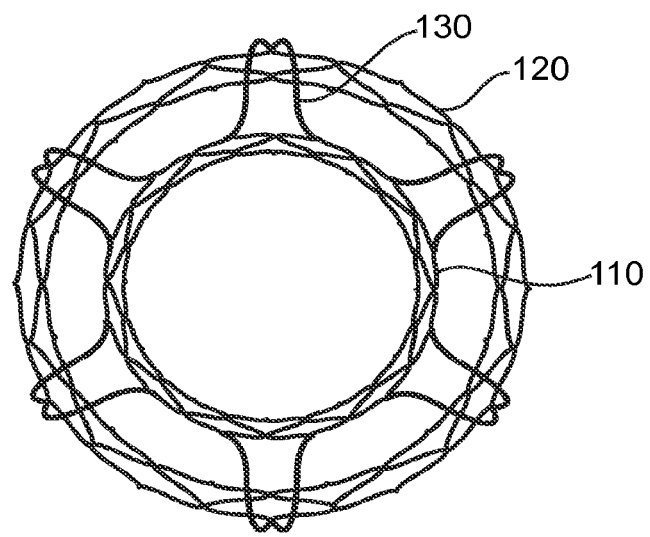
FIG. 2 is a top view of a valve prosthesis frame according to an aspect of this disclosure.
Figure 6:
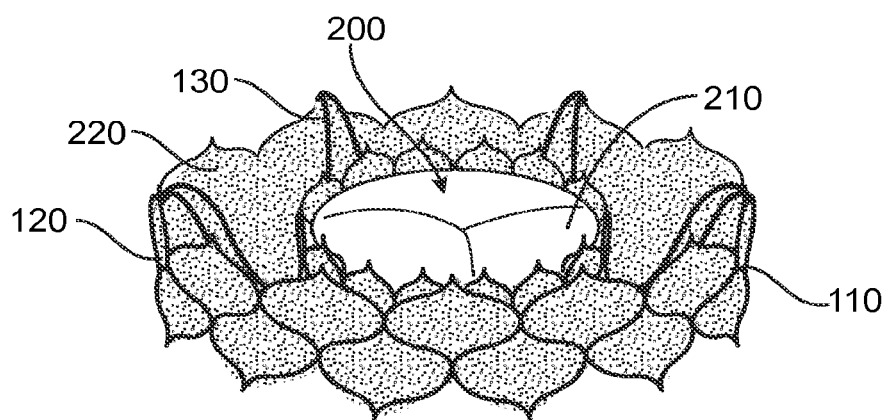
FIG. 6 is a perspective view of a valve prosthesis according to an aspect of this disclosure.
Figure 7:
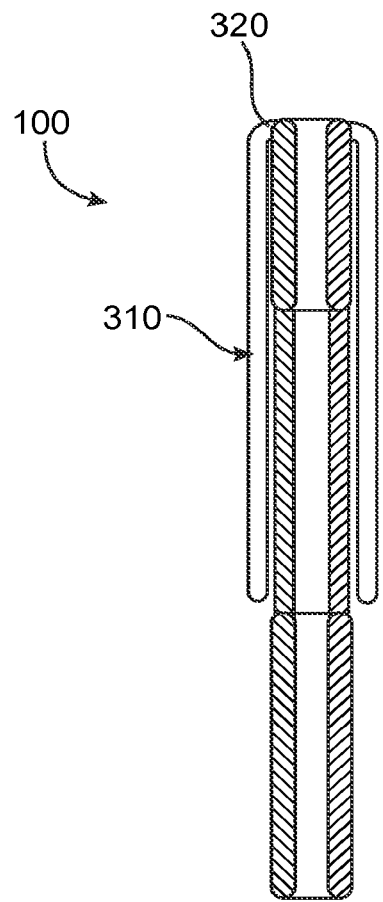
FIG. 7 is a sectional view of a valve prosthesis frame in a collapsed configuration according to an aspect of this disclosure.
Figure 8:
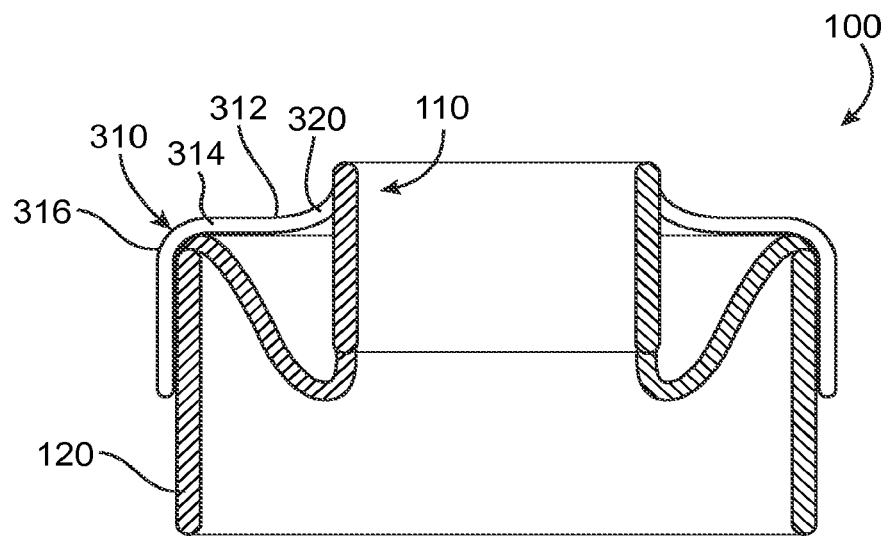
FIG. 8 is a sectional view of a valve prosthesis frame according to an aspect of this disclosure.

Frame 100 is shape set such that upon deployment at a patient's native valve annulus, inner portion 110 moves inside outer portion 120 and remains in that position, as shown in FIGS. 1-2 and 6. In an alternate aspect, outer portion 120 moves to surround inner portion 110. In one aspect of the invention, the entire inner portion 110 is positioned within the interior area of outer portion 120. As disclosed herein, the interior area is defined as the radial and longitudinal space bounded by an inner diameter and a length of a segment of the frame. In this aspect, the longitudinal length of inner portion 110 is less than or equal to the length of outer portion 120. In an alternate aspect of the invention, in the expanded configuration, a section of inner portion 110 is positioned within the interior area of outer portion 120 and a second section of inner portion 110 is positioned outside of the interior area of outer portion 120. In one aspect of the invention, the longitudinal length of inner portion 110 is greater than the longitudinal length of outer portion 120. In this aspect, longer inner portion 110 can be used with relatively longer valve leaflets so as to increase valve durability as compared to a valve prosthesis with shorter valve leaflets.

Positioning inner portion 110 within outer portion 120 reduces the projection distance of frame 100 into the patient's left ventricle. If the left ventricle of a prosthetic valve is too large, the left ventricle flow tract can become obstructed. This obstruction in turn negatively affects how blood flows through the heart and into the aorta. Therefore, a low left ventricle projection distance is desired, as provided by frame 100.

Figure 9:
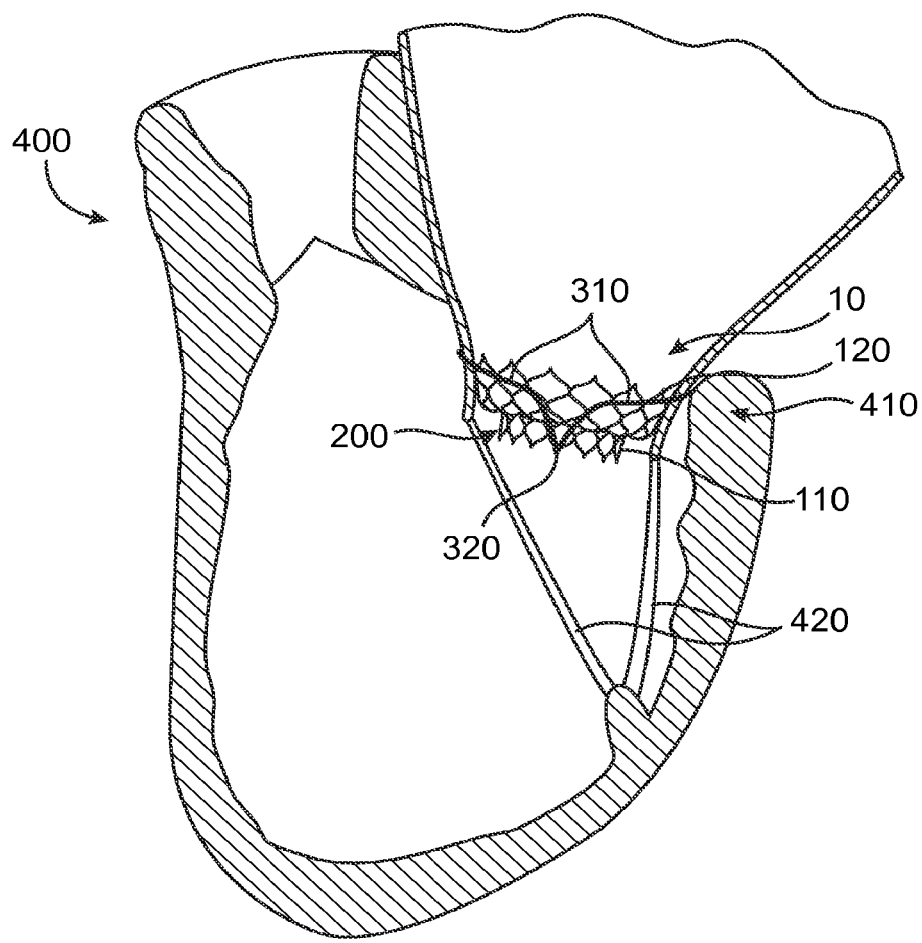
FIG. 9 is a schematic view of a valve prosthesis implanted in the heart according to an aspect of this disclosure.

Referring now to FIGS. 7-12, frame 100 can include one or more engagement arms 310. Engagement arms 310 can be attached to inner portion 110 to anatomically match the native valve leaflets. Upon implantation, outer engagement arms 310 clamp and immobilize the native valve leaflets, and hold the native leaflets close to outer portion 120. As shown in FIG. 9, in one aspect of the disclosure, valve prosthesis 10 can be placed in mitral annulus 410. Proper seating of valve prosthesis 10 at the mitral annulus 410 is achieved by engagement arms 310 capturing the native mitral valve leaflets. The radial force generated by valve prosthesis 10 in the atrium against engagement arms 310 creates a "sandwich effect" by pinching the native mitral valve leaflets and atrial tissue against outer portion 120 of valve prosthesis 10. The native mitral valve leaflet acts as a sealing mechanism around valve prosthesis 10. In addition, engagement arms 310 can add tension onto the native chordae to reduce peri-valvular leakage and increase valve stability.

In one aspect of the invention, engagement arms 310 are attached to inner portion 110 at connection 320. Each engagement arm can include a bend 312, a horizontal component 314, and a second bend 316 in order to better match the native valve anatomy. Horizontal component 314 extends engagement arms 310 in the radial direction. In one aspect of the invention as shown in FIG. 9, valve prosthesis 10 can include two engagement arms 310 to capture the native valve leaflets. Engagement arms 310 are connected to each other and to inner portion 110 at a common point at connection 320.

Figure 10:
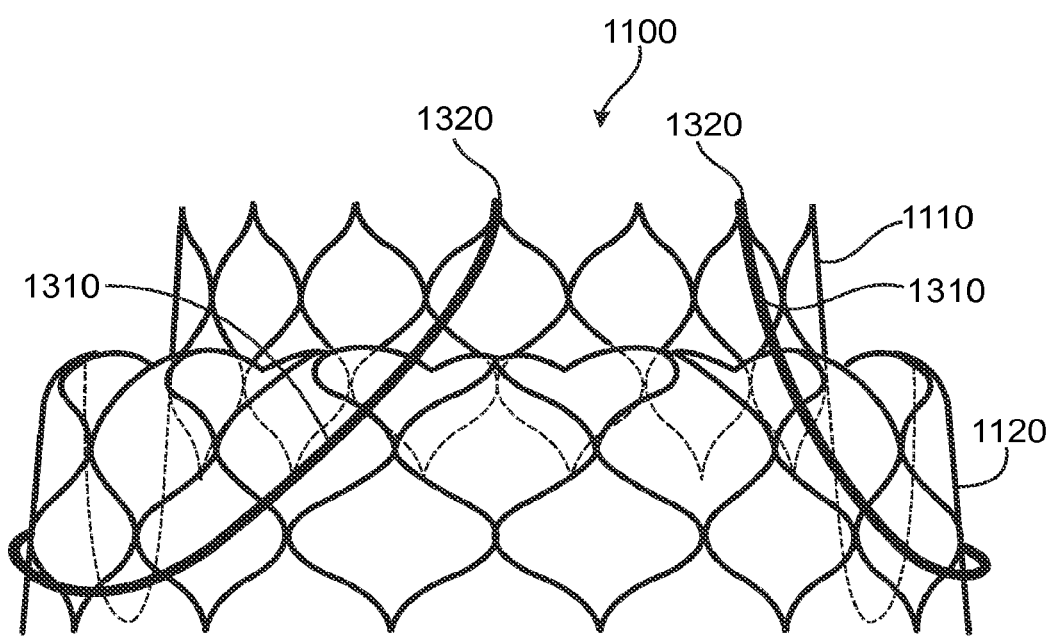
FIG. 10 is a front view of a valve prosthesis frame according to an aspect of this disclosure.

In a further aspect of the invention shown in FIG. 10, each engagement arm 1310 can be connected to inner portion 1110 at a different point such that frame 1100 includes two connections 1320 for each engagement arm 1310. Attaching each engagement arm 1310 to frame 1100 at different connections 1320 reduces the tension imparted onto the native chordae by engagement arms 1310. It is desirable to impart tension onto the native chordae with valve frame engagement arms. However, excessive tension can cause the native chordae to rupture which reduces the effectiveness of the valve prosthesis.

Figure 11:
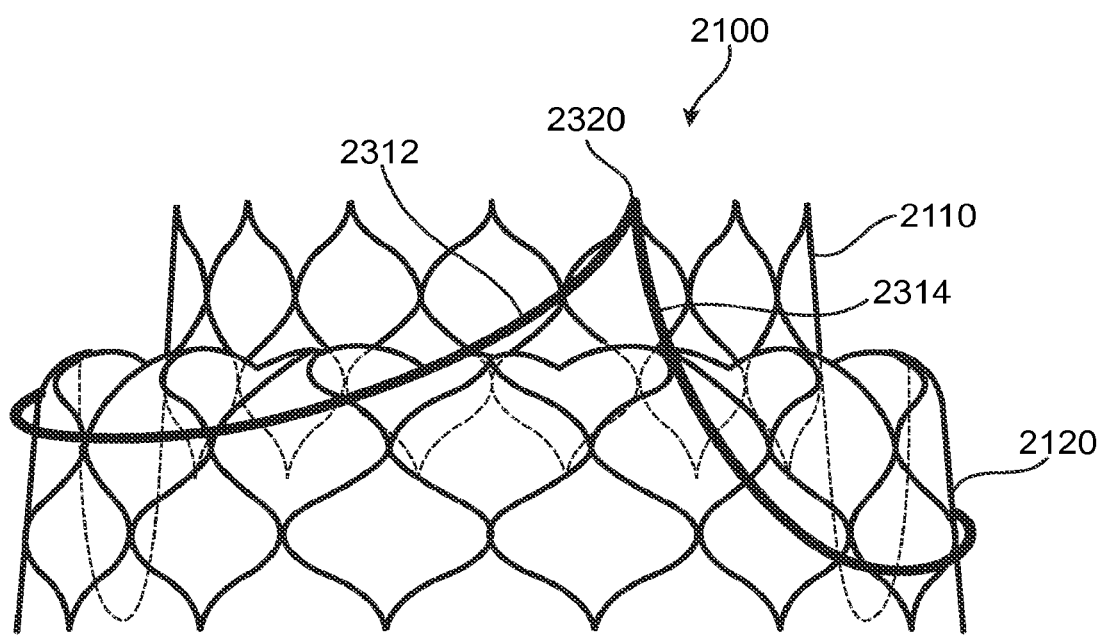
FIG. 11 is a front view of a valve prosthesis frame according to an aspect of this disclosure.
Figure 12:
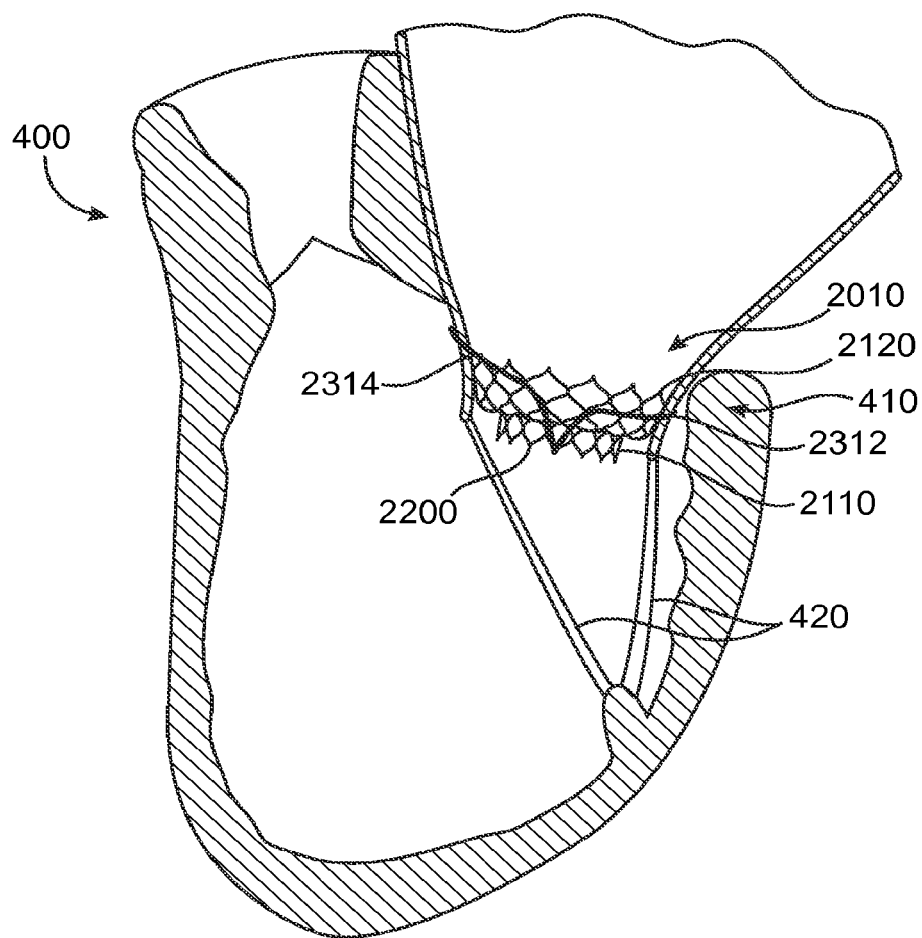
FIG. 12 is a schematic view of a valve prosthesis implanted in the heart according to an aspect of this disclosure.

In a further aspect of the invention shown in FIGS. 11-12, frame 2100 can have engagement arms of varying lengths in the longitudinal direction. This varying length of the engagement arms is provided to accommodate the longer anterior leaflet of the native mitral valve. In this aspect, posterior engagement arm 2312 is shorter in the longitudinal direction than anterior engagement arm 2314. Posterior engagement arm 2312 and anterior engagement arm 2314 can be connected to frame 2100 at connections 2320 on inner portion 2110. As shown, a section of inner portion 2110 is within an interior area of outer portion 2120.

Figure 13:
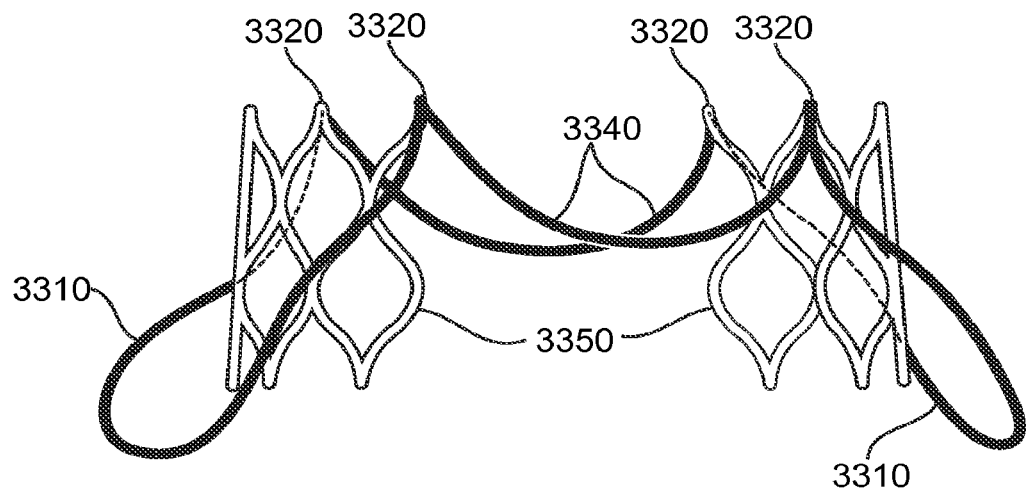
FIG. 13 is an assembly view of a valve prosthesis frame according to an aspect of this disclosure.
Figure 13:
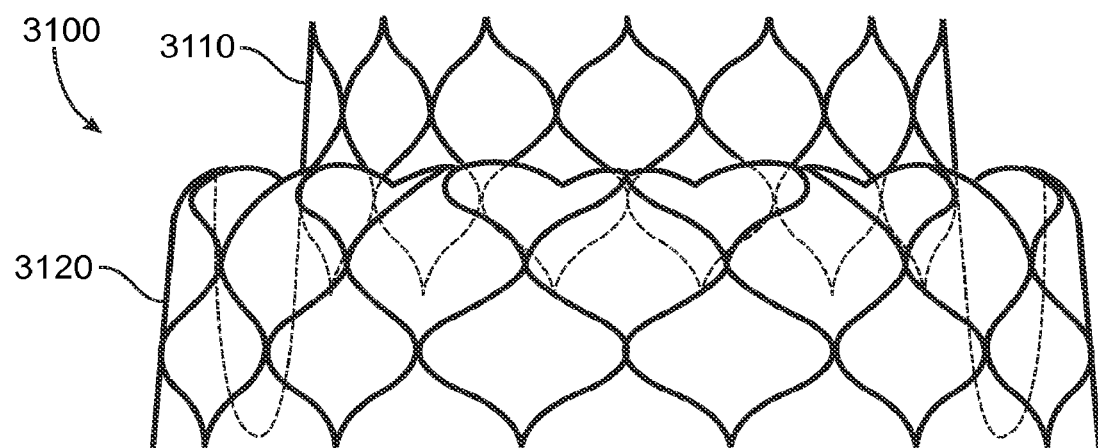
Figure 14:
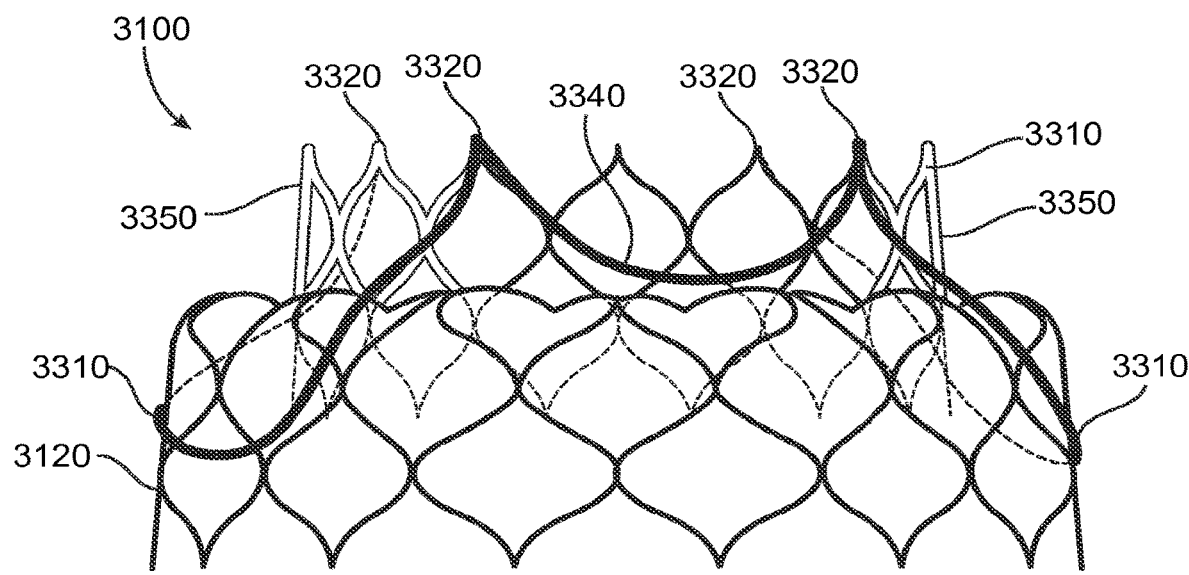
FIG. 14 is a front view of a valve prosthesis frame according to an aspect of this disclosure.
Figure 15:
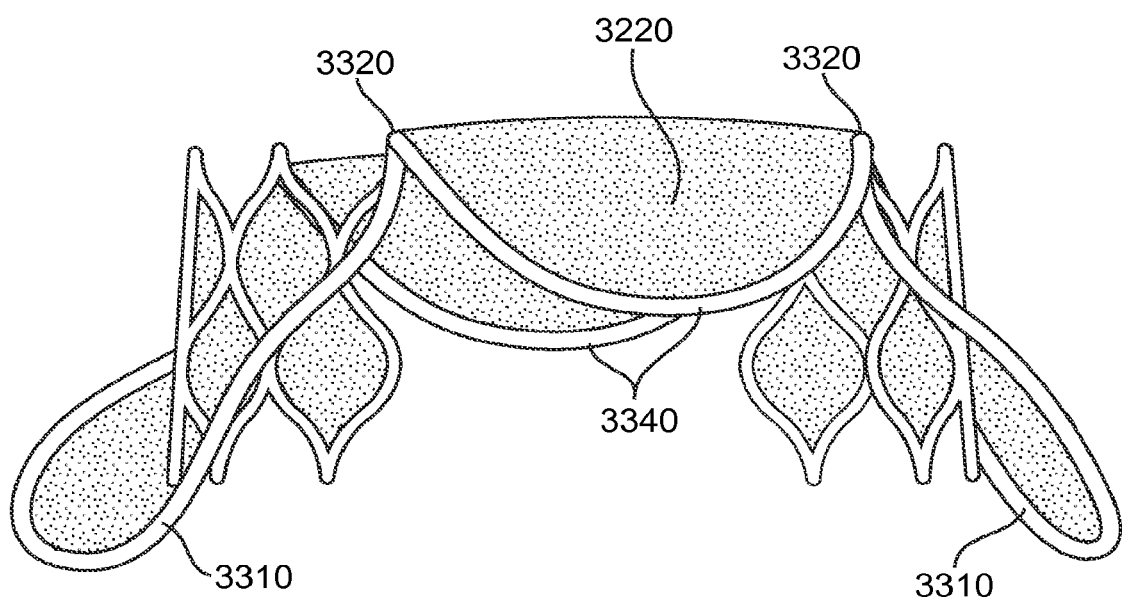
FIG. 15 is a front view of a portion of a valve prosthesis frame according to an aspect of this disclosure.

Referring now to FIGS. 13-15, engagement arms 3310 can include connecting segments 3340 that connect the respective connections 3320 to provide a continuous structure. In this aspect, the continuous engagement arm structure ensures symmetry of engagement arms 3310, simplifies assembly of engagement arms 3310 onto frame 3100, and enhances the overall frame strength. Engagement arms 3310 can also include additional struts 3350 that extend between connections 3320 of each engagement arm 3310. Struts 3350 prevent native valve leaflets from bulging through the engagement arms 3310. In addition, struts 3350 and connecting segments 3340 can make the resulting valve prosthesis assembly stiffer in the radial direction. The stiffer valve prosthesis is better able to maintain a circular expanded cross section against fluid pressures exerted on the valve prosthesis. Maintaining a circular cross section provides better valve performance and increases the longevity of the valve prosthesis.

In a further aspect of the invention, engagement arms 3310, connecting segments 3340, and additional struts 3350 can be covered with a covering 3220. Covering 3220 can be a biocompatible fabric or can be tissue, for example porcine or bovine pericardium. Covering 3220 can prevent the native valve leaflets from bulging through engagement arms 3310, can reduce metal to metal abrasion between engagement arms 3310 and frame 3100, and can protect the native chordae from abrasion against engagement arms 3310. In an alternate aspect of the invention, covering 3220 only covers engagement arms 3310.

Figure 16:
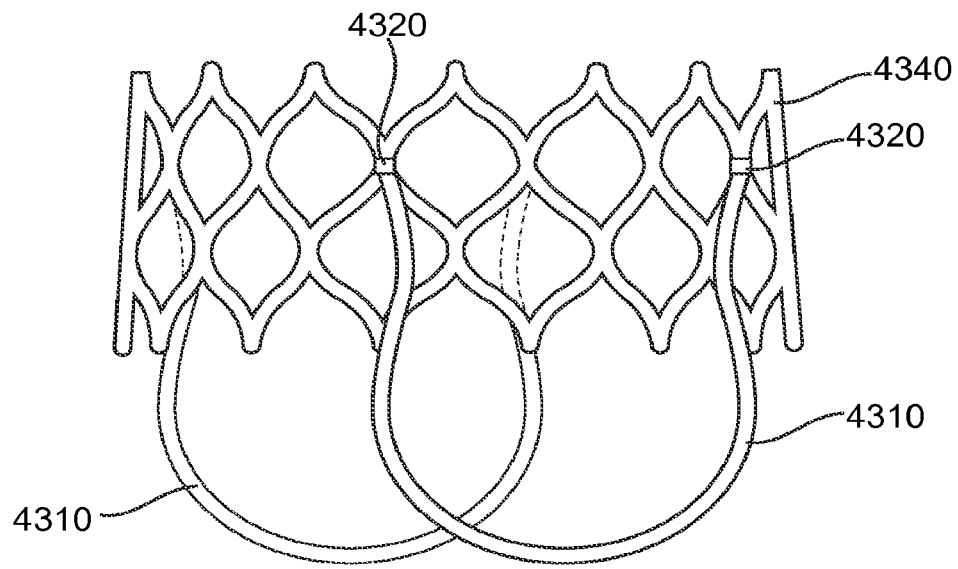
FIG. 16 is an assembly view of a valve prosthesis frame according to an aspect of this disclosure.
Figure 16:
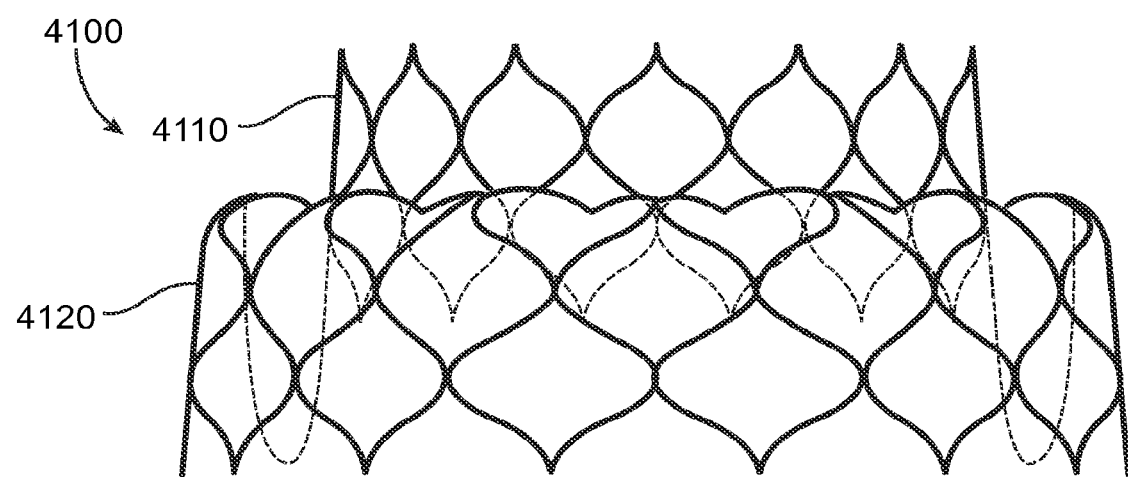

In an alternate aspect of the invention shown in FIG. 16, engagement arms 4313 can be connected to a connecting segment 4340 and can form a continuous arm structure. Connecting segments 4340 can include a series of struts that extend circumferentially and are geometrically identical in structure to the corresponding struts on frame 4100. In this aspect, engagement arms 4310 can be connected to connecting segment 4340 at connections 4320. The continuous arm structure provided by connecting segment 4340 can simplify assembly of the valve prosthesis and enhances the overall strength of frame 4100 in the radial direction. In a further aspect of the invention, engagement arms 4313 and connecting segment 4340 can be covered by a covering (not shown). The covering can be a biocompatible fabric or can be tissue, for example porcine or bovine pericardium.

In a further aspect of the invention, engagement arms can be integrally formed into the valve prosthesis frame.

Implantation of the valve prosthesis will now be described. As discussed above, the valve prosthesis preferably comprises a self-expanding frame that can be compressed to a contracted delivery configuration onto a delivery device. This frame design requires a loading system to crimp valve prosthesis 10 to the delivery size.

The valve prosthesis and inner member can then be loaded into a delivery sheath of conventional design. In one aspect of the invention, valve prosthesis and can be delivered transfemorally. In this aspect, the delivery device and valve prosthesis can be advanced in a retrograde manner through the femoral artery and into the patient's descending aorta. The catheter then is advanced, under fluoroscopic guidance, over the aortic arch, through the ascending aorta, into the left ventricle, and mid-way across the defective mitral valve. Once positioning of the catheter is confirmed, the delivery device can deploy valve prosthesis 10 in the native annulus.

As the valve prosthesis expands, it traps the leaflets of the patient's defective valve against the valve annulus, retaining the native valve in a permanently open state. The outer portion of the valve prosthesis expands against and aligns the prosthesis within the mitral annulus, while the inner portion withdraws into an interior area of the outer portion to reduce the projection of the valve prosthesis into the left ventricle.

Alternatively, the valve prosthesis can be delivered through a transapical procedure. In a transapical procedure, a trocar or overtube is inserted into the left ventricle through an incision created in the apex of a patient's heart. A dilator is used to aid in the insertion of the trocar. In this approach, the native valve (e.g. the mitral valve) is approached from the downstream relative to the blood flow. The trocar is retracted sufficiently to release the self-expanding valve prosthesis. The dilator is preferably presented between the valve leaflets. The trocar can be rotated and adjusted as necessary to properly align the valve prosthesis. The dilator is advanced into the left atrium to begin disengaging the proximal section of the valve prosthesis from the dilator. In the transapical procedure, the inner portion of the frame can be inserted first and the outer portion can then be moved distally such that it sits at the mitral annulus. In this configuration, the back pressure of blood flow from the left ventricle won't cause the inner portion of the frame to be pushed back into its original configuration where the inner portion and outer portion are longitudinally adjacent to each other.

In an alternate aspect of the invention, the valve prosthesis can be delivered through a transatrial procedure. In this procedure, the dilator and trocar are inserted through an incision made in the wall of the left atrium of the heart. The dilator and trocar are advanced through the native valve and into the left ventricle of heart. The dilator is then withdrawn from the trocar. A guide wire is advanced through the trocar to the point where the valve prosthesis comes to the end of the trocar. The valve prosthesis is advanced sufficiently to release the self-expanding frame from the trocar. The trocar can be rotated and adjusted as necessary to properly align the valve prosthesis. The trocar is completely withdrawn from the heart such that the valve prosthesis self-expands into position and assumes the function of the native valve.

The foregoing description has been presented for purposes of illustration and enablement, and is not intended to be exhaustive or to limit the invention to the precise form disclosed. Other modifications and variations are possible in light of the above teachings. The embodiments and examples were chosen and described in order to best explain the principles of the invention and its practical application and to thereby enable others skilled in the art to best utilize the invention in various embodiments and various modifications as are suited to the particular use contemplated. It is intended that the appended claims be construed to include other alternative embodiments of the invention.

What is claimed is:

1. A method of treating a valve disorder in a patient's heart, comprising:
    collapsing a valve prosthesis including a unitary frame and a valve onto a delivery system to place a first portion of the unitary frame longitudinally adjacent to a second portion of the unitary frame, the valve being disposed within the first portion of the unitary frame;
    delivering the delivery system and the valve prosthesis to a heart;
    expanding the valve prosthesis in the heart such that the first portion of the unitary frame moves to be positioned within an interior area of the second portion of the unitary frame; and
    withdrawing the delivery system from the heart.

2. The method of claim 1, wherein the step of expanding includes positioning the entire first portion of the unitary frame within the interior area of the second portion of the unitary frame.

3. The method of claim 1, wherein the first and second portions of the unitary frame are integrally formed and are connected to each other by a third portion of the unitary frame extending between the first portion and the second portion.

4. The method of claim 1, wherein the unitary frame of the valve prosthesis further comprises engagement arms configured to engage native valve leaflets, the engagement arms being connected to the first portion of the unitary frame.

5. The method of claim 4, wherein the step of expanding includes engaging native valve leaflets with the engagement arms of the unitary frame when the valve prosthesis is expanded in the heart.

6. The method of claim 1, wherein the step of expanding includes implanting the second portion of the unitary frame within a native valve annulus of the heart.

7. A method of treating a valve disorder in a patient's heart, comprising:
    collapsing a valve prosthesis including a unitary frame and a valve onto a delivery system to place an inner tubular portion of the unitary frame longitudinally adjacent to an outer tubular portion of the unitary frame, the valve being disposed within the inner tubular portion of the unitary frame, wherein the inner tubular portion is longitudinally separated from the outer tubular portion by a plurality of connecting arms that extend between and connect the inner tubular portion with the outer tubular portion;
    delivering the delivery system and the valve prosthesis to a heart;
    expanding the valve prosthesis in the heart such that the inner tubular portion of the unitary frame moves to be positioned within an interior area of the outer tubular portion such that the outer tubular portion surrounds the inner tubular portion; and
    withdrawing the delivery system from the heart.

8. A method of treating a valve disorder in a patient's heart, comprising:
    collapsing a valve prosthesis including a unitary frame and a valve onto a delivery system to place a first tubular portion of the unitary frame longitudinally adjacent to a second tubular portion of the unitary frame along a longitudinal axis of the unitary frame, the valve being disposed within the first tubular portion of the unitary frame, wherein the first tubular portion is longitudinally separated from the second tubular portion by a third portion that extends between and connects the first tubular portion with the second tubular portion;
    delivering the delivery system and the valve prosthesis to a heart;
    expanding the valve prosthesis in the heart such that the first tubular portion of the unitary frame moves to be positioned within an interior area of the second tubular portion such that the second tubular portion surrounds the first tubular portion and both of the first tubular portion and the second tubular portion extend parallel to the longitudinal axis of the unitary frame with the third portion at least partially radially extending therebetween; and
    withdrawing the delivery system from the heart.

9. The method of claim 8, wherein the step of expanding includes positioning the entire first tubular portion of the unitary frame within the interior area of the second tubular portion of the unitary frame.

10. The method of claim 8, wherein the first tubular portion, the second tubular portion, and the third portion of the unitary frame are integrally formed.

11. The method of claim 8, wherein the unitary frame of the valve prosthesis further comprises a pair of engagement arms configured to engage native valve leaflets, the pair of engagement arms being connected to the first tubular portion of the unitary frame.

12. The method of claim 11, wherein the step of expanding includes engaging native valve leaflets with the pair of engagement arms of the unitary frame when the valve prosthesis is expanded in the heart.

13. The method of claim 11, wherein a first engagement arm of the pair of engagement arms has a longitudinal length that is different from a longitudinal length of a second engagement arm of the pair of engagement arms.

14. The method of claim 8, wherein the step of expanding includes implanting the second tubular portion of the unitary frame within a native valve annulus of the heart.

15. The method of claim 8, wherein the third portion of the unitary frame comprises a plurality of connecting arms having first ends attached to the first tubular portion of the unitary frame and second ends attached to the second tubular portion of the unitary frame.

16. The method of claim 8, wherein each of the first and second tubular portions of the unitary frame includes a plurality of cells that form a cell pattern.

17. The method of claim 8, wherein the third portion of the unitary frame comprises a plurality of V-shaped connecting arms.

18. The method of claim 17, wherein a pair of first ends of each V-shaped connecting arm is attached to the first tubular portion of the unitary frame and wherein a second end of each V-shaped connecting arm is attached to the second tubular portion of the unitary frame.

19. The method of claim 18, wherein each of the first and second tubular portions of the unitary frame includes a plurality of cells that form a cell pattern.

20. The method of claim 8, wherein a longitudinal length of the first tubular portion of the unitary frame is greater than a longitudinal length of the second tubular portion of the unitary frame.

* * * * *